United States Patent
Aubay et al.

(10) Patent No.: US 6,905,814 B1
(45) Date of Patent: Jun. 14, 2005

(54) USE OF FILM-FORMING TITANIUM DIOXIDE DISPERSIONS FOR CLEANING AND DISINFECTING SURFACES, FILM-FORMING TITANIUM DIOXIDE DISPERSIONS

(75) Inventors: Eric Aubay, Le Perreux sur Marne (FR); Thierry Chopin, Saint-Leu la Foret (FR); Cédric Geffroy, Paris (FR); Véronique Guillou, Antony (FR); Corinne Lehaut, Paris (FR)

(73) Assignee: Rhodia Chimie, Boulogne Billancourt Cedex ( * ) Notice: Subject to any disclaimer, the term of this patent is extended or adjusted under 35 U.S.C. 154(b) by 0 days.

(21) Appl. No.: 09/890,944

(22) PCT Filed: Feb. 15, 2000

(86) PCT No.: PCT/FR00/00371

§ 371 (c)(1),
(2), (4) Date: Dec. 4, 2001

(87) PCT Pub. No.: WO00/49119

PCT Pub. Date: Aug. 24, 2000

(30) Foreign Application Priority Data

Feb. 17, 1999 (FR) .............................................. 99 01938

(51) Int. Cl.$^7$ .......................... C01G 23/047; C09C 1/36
(52) U.S. Cl. ...................... 430/947; 427/214; 427/217; 502/242; 502/309; 502/350; 106/287.19; 106/436; 423/610; 510/382
(58) Field of Search ................................. 427/217, 214; 430/947; 502/309, 242, 350; 423/610; 106/436, 287.19; 510/382

(56) References Cited

U.S. PATENT DOCUMENTS

| | | | | |
|---|---|---|---|---|
| 5,616,532 A | * | 4/1997 | Heller et al. ................. 502/242 |
| 5,753,322 A | * | 5/1998 | Yamaguchi et al. ........... 428/14 |
| 5,853,866 A | * | 12/1998 | Watanabe et al. ......... 428/312.8 |
| 5,961,843 A | * | 10/1999 | Hayakawa et al. .......... 210/748 |
| 6,107,241 A | * | 8/2000 | Ogata et al. ................. 502/350 |
| 6,340,711 B1 | * | 1/2002 | Ohmori et al. ................ 516/79 |
| 6,355,308 B1 | * | 3/2002 | Sato et al. ................ 427/419.8 |
| 6,429,169 B1 | * | 8/2002 | Ichinose ...................... 502/350 |
| 6,479,031 B2 | * | 11/2002 | Ohmori et al. .............. 423/610 |

FOREIGN PATENT DOCUMENTS

| | | | |
|---|---|---|---|
| CA | 2260803 | 1/1998 | ............. C09K/3/18 |
| EP | 857 770 | 8/1998 | ......... C09D/183/04 |
| FR | 2 729 673 | 7/1996 | ............. C11D/3/12 |
| FR | 2 766 494 | 1/1999 | ........... C08L/83/04 |

OTHER PUBLICATIONS

International Search Report.

* cited by examiner

Primary Examiner—Charles Boyer

(57) ABSTRACT

The invention concerns the use of a film-forming titanium dioxide dispersion for cleaning and disinfecting surfaces exposed to light, by depositing a film of titanium dioxide nanoparticles on said surfaces, the continuous phase of said dispersion comprising water and/or at least an alcohol with boiling point at less than 120° C., said dispersion having, when it comprises water, a pH different by at least 1 unit of the value of the titanium dioxide isoelectric pH in said dispersion. The invention also concerns a film-forming titanium dioxide dispersion further comprises a film-forming polymer. The invention further concerns a method for cleaning and disinfecting surfaces exposed to light which consists in depositing and then drying on said surfaces a titanium oxide film-forming dispersion.

22 Claims, No Drawings

USE OF FILM-FORMING TITANIUM DIOXIDE DISPERSIONS FOR CLEANING AND DISINFECTING SURFACES, FILM-FORMING TITANIUM DIOXIDE DISPERSIONS

This aplication is an application under 35 U.S.C. 371 of International Application Number PCT/FR00/00371 filed on Feb. 15, 2000.

The present invention relates to the use of a film-forming dispersion of titanium dioxide nanoparticles for cleaning and/or disinfecting surfaces exposed to light. The invention also relates to a process for cleaning and/or disinfecting surfaces exposed to light by depositing on said surfaces a film of titanium dioxide nanoparticles, and to titanium dioxide nanoparticle dispersions whose film-forming properties are improved by the presence of a film-forming polymer.

The use of titanium dioxide nanoparticles as a bactericidal and photooxidizing agent in detergent compositions for the washing of laundry or of surfaces was described by the Applicant in its French patent application No. 95 00821 of Jan. 25, 1996.

The Applicant has observed that titanium dioxide nanoparticle dispersions are film-forming.

The object of the present invention is to utilize the photooxidizing properties of titanium dioxide nanoparticles and their film-forming nature to clean and/or disinfect surfaces on said surfaces of an impermanent film of titanium dioxide capable under light of generating free radicals which disinfect the surfaces and oxidize the soiling.

The creation of this film makes it possible
to clean (remove soiling)
to control or even suppress bacterial proliferation between two operations of disinfecting by conventional means;
to reduce the frequency of cleaning or disinfection and/or the quantity of cleaning or disinfecting products presently used.

The film formed is then progressively removed by the subsequent cleaning steps. The target fields of application may be very varied, such as the cleaning or disinfecting of hard surfaces encountered in the food industry, kitchens, bathrooms, washrooms, hospitals, glazing, facades, etc, and also the breakdown and/or removal of heavy hydrocarbons deposited on surfaces, particularly following accidental pollution (for example beaches, rocks, equipment, plants, etc).

The invention first provides for the use of a titanium dioxide dispersion for cleaning and/or disinfecting surfaces exposed to light by deposition of a film of titanium dioxide on said surfaces, said titanium dioxide being in the form of elementary particles whose size is less than 100 nm, preferably less than 70 nm, and whose specific surface area is greater than 150 m$^2$/g, preferably greater than 200 m$^2$/g, the continuous phase of said dispersion comprising water and/or at least one alcohol whose boiling point is less than 120° C., preferably less than or equal to 100° C., said dispersion having, when it comprises waters, a pH different by at least 1 unit, preferably by at least 2 units, from the value of the isoelectric point of titanium dioxide in said dispersion.

The pH of the dispersion comprising water is of course the pH of the continuous phase.

The titanium dioxide employed is very particularly in the form of elementary particles whose size is of the order of from 20 to 60 nm and whose specific surface area is of the order of from 200 to 300 m$^2$/g.

The specific surface area given is a BET surface. By BET surface is meant the specific surface area determined by nitrogen adsorption in accordance with the standard ASTM D 3663-78, based on the Brunauer —Emmett—Teller method described in the journal "The Journal of the american Society",60, 309 (1938). The size of the elementary particles of titanium dioxide according to the invention is measured by transmission electron microscopy (TEM).

The nature of the elementary particles of titanium dioxide is preferably anatase (isoelectric point between 5.5 and 6 for pure anatase). Within said dispersion, said elementary particles may be present in the form of both aggregates and elementary particles.

For effective implementation of the invention, said dispersion may comprise in the order of from 0.01 to 15% of its weight, preferably in the order of from 0.1 to 10% of its weight, of titanium dioxide.

Among the alcohols which may constitute or be present in the continuous phase, mention may be made in particular of aliphatic monoalcohols whose boiling point is less than 100° C. such as ethanol, isopropanol, etc.

When the continuous phase consists of a water/alcohol(s) mixture whose boiling point is less than 120° C., the ratio between the water and the alcohol or alcohols is arbitrary. A high boiling point alcohol (in particular a diol such as ethylene glycol) may, however, be present in the continuous phase, but may not represent more than 10% of the weight of said phase.

Preferentially, the continuous phase comprises water, preferably from 50 to 100%, preferably from 70 to 99.9% of its weight of water.

When the continuous phase comprises water, the pH values favorable to effective implementation of the invention may range from 0 to 14, preferably from 2 to 14, and are a function of other additives which may be present in the dispersion and capable of modifying the isoelectric point of the titanium dioxide.

When no additive capable of modifying the isoelectric point of titanium dioxide is present, the pH values favorable to effective implementation of the invention are situated below 4 or above 8; preferentially, the pH of the dispersion may range from 0 to 3 approximately or from 9 to 14 approximately.

If necessary, pH regulators may be present; mention may be made of mineral acids or organic acids such as hydrochloric, nitric, sulfuric, phosphoric, citric, glutaric, adipic and succinic acids, etc., and bases such as aqueous ammonia, alkali metal hydroxides, sodium carbonate, and triethanolamine, etc.

Said dispersion may further comprise other additives which are soluble or dispersible in the continuous phase, said additives possibly promoting its stability, wettability, augmenting its film-forming nature, its biocidal nature, or providing other supplementary properties.

Examples of additives which may be mentioned include:
nonionic surfactants promoting wettability, of the polyoxyethylenated $C_6$–$C_{12}$ alkylphenol type, polyoxypropylenated and/or polyoxyethylenated $C_8$–$C_{22}$ aliphatic alcohol type, ethylenedioxide-propylene oxide block copolymers, optionally polyoxyethylenated carboxylic amides, etc,
anionic or amphoteric surfactants as dispersants, of the alkali metal soap type (alkali metal salts of $C_8$–$C_{24}$ fatty acids), alkali metal sulfonates ($C_8$–$Cl_{13}$ alkylbenzene sulfonates, $C_{12}$–$C_{16}$ alkylsulfonates), sulfated and oxyethylenated $C_6$–$C_{16}$ fatty alcohols, sulfated and oxyethylenated $C_8$–$C_{13}$ alkylphenols type, alkali metal sulfosuccinates ($C_{12}$–$C_{16}$ alkylsulfo-succinates) etc, betaines, etc
biocides or bacteriostatics capable of improving the biocidal nature of the dispersions, especially in the case of inadequate lighting, such as cationic surfactants (alkyldimethylammonium halides, etc), quaternary ammonium or phosphonium halide biocides, glycine-derivative amphoteric biocides, phenolic biocides, chlorhexidine-derivative biocides, hypochlorites, quaternary polyammonium film-forming polymers or biocides, etc film-forming antisoiling agents such as optionally sulfonated terephthalic polyesters, etc other film-forming homopolymers or copolymers such as those derived from monomers containing ethylenic unsaturation, especially cationic or amphoteric homopolymers or copolymers derived from cationic monomers containing ethylenic unsaturation film-forming polyoxyalkylene polymers which carry anionic functions film-forming polymers which impart brightness and oleophobicity, such as polyalkoxylated organopolysiloxanes, etc.

fragrances dyes, etc.

These various additives may be present in a proportion of from 0 to 15% by weight of said dispersion, One particular embodiment of the invention consists in improving the film-forming nature of the titanium dioxide nanoparticles by the presence within the dispersion of at least one organic or organosiloxane polymer of film-forming nature which may further impart one or more supplementary properties to said dispersion.

The amount of polymer that may be present may represent in the order of from 0.005 to 15%, preferably in the order of from 0.01 to 10% of the weight of said dispersion.

Among the film-forming organic or organosiloxane polymers that may be employed, very particular mention may be made of:

terephthalic polyesters additionally exhibiting antisoiling properties, such as polyester copolymers based on ethylene terephthalate and/or propylene terephthalate and polyoxyethylene terephthalate units (U.S. Pat. Nos. 3,959,230, 3,893,929, 4,116,896, 4,702,857, 4,770,666);

sulfonated polyester oligomers obtained by sulfonating an ethoxylated allyl alcohol-derived oligomer, dimethyl terephthalate and 1,2-propylenediol (U.S. Pat. No. 4,968, 451)

polyester copolymers based on propylene terephthalate and polyoxyethylene terephthalate units and terminated with ethyl or methyl units (U.S. Pat. No. 4,711,730) or polyester oligomers terminated with alkylpolyethoxy groups (U.S. Pat. No. 4,702,857) or anionic sulfopolyethoxy (U.S. Pat. No. 4,721,580) or sulfoaroyl groups (U.S. Pat. No. 4,877,896)

polyester-polyurethanes obtained by reacting a polyester obtained from adipic acid and/or terephthalic acid and/or sulfoisophthalic acid and a diol with a prepolymer containing terminal isocyanate groups obtained from a polyoxyethylene glycol and a diisocyanate (FR-A-2 334 698)

sulfonated polyester oligomers obtained by condensing isophthalic acid, dimethyl sulfosuccinate and diethylene glycol (FR-A-2 236 926)

polyester copolymers derived from dimethyl terephthalate, isophthalic acid, dimethyl sulfoisophthalate and ethylene glycol (EP-A-540374) -cationic polymers further exhibiting bacteriostatic properties, such as the quaternary ammonium ionenes described in U.S. Pat. No. 4,157,388 (MIRAPOL A-15 or POLYQUATERNIUM-2 from Rhodia)

cationic polymers derived from epichlorohydrin and dimethylamine and those derived from epichlorohydrin and imidazole, such as GLOKILL PQ and ELC from Rhodia film-forming cationic or amphoteric homopolymers or copolymers derived from cationic monomers containing ethylenic unsaturation (described in more detail below)

film-forming polyoxyalkylene polymers which carry anionic functions, such as copolymers of acrylic acid and/or methacrylic acid and polyethylene glycol acrylate and/or methacrylate whose polyoxyethylene unit has a mass of the order of from 500 to 10,000 polyalkoxylated polydimethylsiloxanes which impart brightness and oleophobicity, such as SILICONE COPOLYOL 10646 from Rhodia other film-forming polymers derived from ethylenically unsaturated monomers polymerizable by radical means, such as (meth)acrylic acid, $C_1$–$C_4$ alkyl (meth)acrylates, styrene, butadiene, etc.

One very particularly advantageous embodiment of the invention consists in the use of titanium dioxide dispersions further comprising a film-forming organic polymer which is preferably hydrophilic and is capable of interacting with the surface of the titanium dioxide particles, preferably by electrostatic bonding.

Said dispersions are preferably aqueous and have a pH of the order of from 4 to 9.

They may comprise in the order of from 0.005 to 10%, preferably from 0.01 to 5%, very particularly from 0.01 to 2% by weight of film-forming organic polymer.

Among the film-forming polymers which may be present, mention may be made of:

the sulfonated terephthalic copolyesters or oligoesters already mentioned above film-forming polyoxyalkylene polymers which carry anionic functions, such as copolymers of acrylic acid and/or methacrylic acid and polyethylene glycol acrylate and/or methacrylate whose polyoxyethylene unit has a mass of the order of from 500 to 10,000 film-forming cationic polymers additionally exhibiting bacteriostatic properties, such as the quaternary ammonium ionenes described in U.S. Pat. No. 4,157,388 (MIRAPOL A-15 or POLYQUATERNIUM-2 from Rhodia)

cationic polymers derived from epichlorohydrin and dimethylamine and those derived from epichlorohydrin and imidazole, such as GLOKILL PQ and ELC from Rhodia film-forming cationic or amphoteric homopolymers or copolymers derived from cationic monomers containing ethylenic unsaturation.

By way of example of cationic film-forming homopolymers or copolymers derived from cationic monomers containing ethylenic unsaturation, mention may be made from those derived from at least one of the following cationic monomers aminoacryloyl or -acryloyloxy monomers such as trimethylaminopropyl methacrylate chloride, trimethylaminoethylacrylamide or -methacrylamide chloride or bromide, trimethylaminobutylacrylamide or -methacrylamide methyl sulfate, trimethylaminopropyl-methacrylamide methyl sulfate (MES), (3-methacrylamidopropyl) trimethylammonium chloride (MAPTAC), (3-acrylamidopropyl)trimethylammonium chloride (APTAC), methacryloyloxyethyl trimethylammonium chloride or methyl sulfate, and acryloyloxyethyltrimethylammonium chloride;

1-ethyl-2-vinylpyridinium bromide, chloride or methyl sulfate;

N,N-dialkyldiallylamine monomers such as N,N-dimethyldiallylammonium chloride (DADMAC);
polyquaternary monomers such as dimethylaminopropylmethacrylamide chloride, N-(3-chloro-2-hydroxypropyl)trimethylammonium (DIQUAT), etc;
optionally in a mixture with at least one nonionic monomer such as acrylamide, N-isopropylacrylamide, N,N-dimethylacrylamide, dimethylaminoethylmethacrylate (DMAEMA), dimethylaminopropylmethacrylamide, vinyl alcohol, alkyl or hydroxyalkyl acrylates or methacrylates, polyoxyalkylene glycol acrylates or methacrylates, etc.

Very particular mention may be made of DIQUAT homopolymers, such as MIRAPOL CLASTA from Rhodia, and DADMAC homopolymers, such as MIRAPOL 100 from Rhodia.

By way of example of amphoteric film-forming copolymers derived from cationic monomers containing ethylenic unsaturation, mention may be made of those derived from at least one of the abovementioned cationic monomers and at least one anionic monomer such as
acrylic, methacrylic, fumaric, maleic, itaconic, N-methacroylalanine, N-acryloylhydroxyglycine, etc, acids or anhydrides, or their water-soluble salts;
water-soluble sulfonated or phosphonated ethylenically unsaturated monomers, such as sulfopropyl acrylate or its water-soluble salts, water-soluble styrene sulfonates, vinylsulfonic acid and its water-soluble salts or vinylphosphonic acid and its water-soluble salts, etc;
optionally in a mixture of at least one nonionic monomer such as acrylamide, N-isopropylacrylamide, N,N-dimethylacrylamide, dimethylaminoethylmethacrylate (DMAEMA), dimethylaminopropylmethacrylamide, vinyl alcohol, alkyl or hydroxyalkyl acrylates or methacrylates, polyoxyalkylene glycol acrylates or methacrylates, etc.

Very particular mention may be made of the following copolymers or terpolymers:
MAPTAC/acrylic or methacrylic acid; DIQUAT/acrylic or methacrylic acid; DADMAC/acrylic or methacrylic acid;
MES/acrylic or methacrylic acid/DMAEMA;
MAPTAC/acrylic acid/acrylamide; MAPTAC/maleic anhydride/acrylamide; MAPTAC/vinylsulfonic acid/acrylamide;
DADMAC/acrylic acid/acrylamide; DADMAC/maleic anhydride/acrylamide; DADMAC/vinylsulfonic acid/acrylamide;
DIQUAT/acrylic acid/acrylamide; DIQUAT/maleic anhydride/acrylamide; DIQUAT/vinylsulfonic acid/acrylamide;
with a ratio of the total number of anionic charges to the total number of cationic charges of from 95/5 to 5/95, very particularly from 90/10 to 10/90.

Said cationic or amphoteric film-forming homopolymers or copolymers derived from cationic monomers containing ethylenic unsaturation preferably have a molecular mass of less than 100,000 (molecular mass by weight, expressed in g/mol, determinable by aqueous gel permeation chromatography (GPC) or measurement of the viscosity in IN $NaNO_3$ solution.

The invention secondly provides a film-forming dispersion comprising
in the order of from 0.01 to 15% of its weight, preferably in the order of from 0.1 to 10% of its weight of titanium dioxide in the form of elementary particles whose size is less than 100 nm, preferably less than 70 nm, and whose specific surface area is greater than 150 $m^2/g$, preferably greater than 200 $mg^2/g$,
and in the order of from 0.005 to 15% of its weight, preferably in the order of from 0.01 to 10% of its weight, of at least one film-forming polyalkoxylated organosiloxane or organic polymer,
the continuous phase of said dispersion comprising water and/or at least one alcohol whose boiling point is less than 120° C., preferably less than or equal to 100° C., and having, when it comprises water, a pH different by at least 1 unit, preferably at least 2 units, from the value of the isoelectric point of titanium dioxide in said dispersion.

Preferential or more particular features regarding the nature of the titanium dioxide, the continuous phase, pH regulators, other additives that may be present, and respective amounts of various components, have already been indicated above.

Examples of film-forming alkoxylated organosiloxane or organic polymers which may be employed to improve the film-forming nature of the titanium nanoparticles have already been mentioned above.

Said dispersion may be obtained by mixing its various components at ambient temperature.

An especially advantageous film-forming dispersion comprises
in the order of from 0.01 to 15% of its weight, preferably in the order of from 0.1 to 10% of its weight of titanium dioxide in the form of elementary particles whose size is less than 100 nm, preferably less than 70 nm, and whose specific surface area is greater than 150 $m^2/g$, preferably greater than 200 $m^2/g$,
and in the order of from 0.005 to 10% of its weight, preferably in the order of from 0.01 to 5%, more particularly from 0.01 to 2% of its weight, of at least one film-forming organic polymer which is preferably hydrophilic and is capable of interacting with the surface of the titanium dioxide particles, preferably by electrostatic bonding,
the continuous phase of said dispersion comprising water and/or at least one alcohol whose boiling point is less than 120° C., preferably less than or equal to 100° C., and having, when it comprises water, a pH different by at least 1 unit, preferably at least 2 units, from the value of the isoelectric point of titanium dioxide in said dispersion.

They are preferably aqueous and have a pH of the order of from 4 to 9.

Examples of film-forming organic polymers which may be employed for interacting with the surface of the titanium dioxide particles, preferably by electrostatic bonding, have already been stated above.

The invention lastly provides a process for cleaning and/or disinfecting surfaces exposed to light by depositing and then drying on said surfaces a film-forming titanium dioxide dispersion, said titanium dioxide being in the form of elementary particles whose size is less than 100 nm, preferably less than 70 nm, and whose specific surface area is greater than 150 $m^2/g$, preferably greater than 200 $m^2/g$, the continuous phase of said dispersion comprising water and/or at least one alcohol whose boiling point is lower than 120° C., preferably lower than or equal to 100° C., said dispersion having, when it comprises water, a pH different by at least 1 unit, preferably by at least 2 units, from the value of the isoelectric point of titanium dioxide in the dispersion.

Preferential or more particular features regarding the nature of the titanium dioxide, the continuous phase, pH regulators, other additives that may be present, especially film-forming polymers, and respective amounts of various components, have already been mentioned above.

The titanium dioxide nanoparticle dispersion may be deposited on these surfaces by fine spraying onto the surface to be treated, by application with the aid of a sponge, a cloth or with the aid of a preimpregnated cellulosic material, or any other means, in such a way as to deposit in the order of from 0.01 to 10 g of titanium dioxide per $m^2$ of the surface to be treated, preferably in the order of from 0.05 to 5 g of titanium dioxide per $m^2$ of the surface to be treated.

The examples which follow are given by way of illustration.

EXAMPLE 1

A dispersion is prepared of titanium dioxide (anatase) in the form of elementary particles of 40 nm whose specific surface area is 250 $m^2/g$ after drying at 200° C., in a water/alcohol mixture, whose composition is as follows:

| | |
|---|---|
| 15% dispersion of titanium dioxide (anatase) in ethylene glycol | 3% |
| REPEL O TEX QCJ (15% aqueous dispersion of film-forming antisoiling ethylene terephthalate/polyoxyethylene terephthalate copolymer) | 13% |
| isopropanol | 47.5% |
| deionized water | 36.5% | by introducing the film-forming antisoiling copolymer into the dispersion of titanium dioxide in ethylene glycol, followed by addition of the water/isopropanol mixture and then adjustment of the pH to 2.5 using hydrochloric acid.

EXAMPLE 2

A dispersion is prepared of titanium dioxide (anatase) in the form of elementary particles of 40 nm whose specific surface area is 250 $m^2/g$ after drying at 200° C., in a water/alcohol mixture, whose composition is as follows:

| | |
|---|---|
| 15% colloidal aqueous dispersion of titanium dioxide (anatase) | 3% |
| REPEL O TEX QCJ (15% aqueous dispersion of film-forming antisoiling ethylene terephthalate/polyoxyethylene terephthalate copolymer) | 3% |
| isopropanol | 47% |
| deionized water | 47% | by introducing the film-forming antisoiling copolymer into the colloidal aqueous dispersion of titanium dioxide, followed by addition of the water/isopropanol mixture and then adjustment of the pH to 2.5.

EXAMPLE 3

A dispersion is prepared of titanium dioxide (anatase) in the form of elementary particles of 40 nm whose specific surface area is 250 $m^2/g$ after drying at 200° C., in a water/alcohol mixture, whose composition is as follows:

| | |
|---|---|
| 15% colloidal aqueous dispersion of titanium dioxide | 25% |
| REPEL O TEX QCJ (15% aqueous dispersion of film-forming antisoiling ethylene terephthalate/polyoxyethylene terephthalate copolymer) | 8.3% |
| Isopropanol | 33.3% |
| Deionized water | 33.4% | by introducing the film-forming antisoiling copolymer into the colloidal aqueous dispersion of titanium dioxide, followed by addition of the water/isopropanol mixture and then adjustment of the pH to 2.5.

EXAMPLE 4

A dispersion is prepared of titanium dioxide (anatase) in the form of elementary particles of 40 nm whose specific surface area is 250 $m^2/g$ after drying at 200° C., in a water/alcohol mixture, whose composition is as follows:

| | |
|---|---|
| 15% colloidal aqueous dispersion of titanium dioxide | 3% |
| SILICONE COPOLYOL 10646 (film-forming polyalkoxylated polydimethylsiloxane) | 0.5% |
| isopropanol | 47% |
| deionized water | 49.5% | by introducing the film-forming polymer (imparting brightness and oleophobicity) into the colloidal aqueous dispersion of titanium dioxide, followed by addition of the water/isopropanol mixture and then adjustment of the pH to 2.5.

EXAMPLE 5

A dispersion is prepared of titanium dioxide (anatase) in the form of elementary particles of 40 nm whose specific surface area is 250 $m^2/g$ after drying at 200° C., in a water/alcohol mixture, whose composition is as follows:

| | |
|---|---|
| 15% colloidal aqueous dispersion of titanium dioxide | 25% |
| GLOKILL PQ (50% by weight aqueous solution of film-forming bacteriostatic cationic polymer diluted to 15%) | 8.3% |
| isopropanol | 33.3% |
| deionized water | 33.4% | by introducing the bacteriostatic film-forming polymer into the colloidal aqueous dispersion of titanium dioxide, followed by addition of the water/isopropanol mixture and then adjustment of the pH to 2.5.

EXAMPLE 6

A dispersion is prepared of titanium dioxide (anatase) in the form of elementary particles of 40 nm whose specific surface area is 250 $m^2/g$ after drying at 200° C., in a water/alcohol mixture, whose composition is as follows:

| Reference | A | B |
|---|---|---|
| 15% colloidal aqueous dispersion of titanium dioxide | 3% | 3% |
| GLOKILL PQ (cationic polymer) | 0.1% | 0% |
| isopropanol | 5% | 5% |
| deionized water | 91.9% | 92% |

The pH of the dispersion is subsequently adjusted by adding sodium hydroxide to pH =6.5. In the presence of cationic polymer (test A) the dispersion remains homogeneous and the particle size measurement by laser scattering confirms the absence of aggregation of titanium dioxide (particle size: 40 nm). In the case of the solution without cationic polymer (test B) severe precipitation is observed when sodium hydroxide is added.

The two neutralized solutions A and B are deposited on a black ceramic tile with the aid of adsorbent paper. The amount deposited is of the order of 0.5 mg/cm$^2$.

After drying in the open air, the solution A gives a layer of titanium invisible to the eye. In contrast, solution B gives very distinct white marks. Observation by optical microscopy confirms that the polymer allows an effective state of dispersion to be obtained during drying.

A model soil, stearic acid, is subsequently deposited on each ceramic tile which had been treated before and with formulas A and B. The layer of stearic acid is of approximately 0.01 mg/m$^2$ and it is obtained by depositing a it solution in isopropanol. After drying, the tiles are exposed to visible light for 48 hours.
Following exposure, the ceramic tile treated with solution A has virtually no trace of stearic acid visible to the eye.
The tile treated with solution B exhibits visible traces of stearic acid.

EXAMPLE 7

On a ceramic tile, a film corresponding to 3 or 6 g of titanium dioxide per m$^2$ of tile surface is formed by-spreading the dispersion from example 2 over said tile using a film-drawing device.
The film is left to dry in ambient air overnight. A suspension of bacteria (Pseudomonas Aeruginosa) is deposited over the entire surface of the tile. The tile, covered with a UV-impervious cover (for the purpose of preventing excessive dehydration of the bacteria), is exposed to UV light (365 nm) for 6 hours. The number of colonies is counted and compared with that obtained by depositing the same bacteria suspension on an untreated tile.
The results obtained are as follows:

| Sample | Titanium dioxide deposited (g/m$^2$) | Number of colonies (cfu/ml) |
| --- | --- | --- |
| Untreated tile | — | 5 × 10$^7$ |
| Treated tile | 3 | <10 |
| Treated tile | 6 | <10 |

What is claimed is:

1. A process for cleaning or disinfecting surfaces exposed to light, comprising the step of depositing a film of titanium dioxide on said surfaces with a film-forming dispersion comprising a continuous phase, said titanium dioxide being in the form of elementary particles whose size is less than 100 nm, and whose specific surface area is greater than 150 m$^2$/g, the continuous phase of said dispersion comprising water or at least one alcohol whose boiling point is less than 120° C., and said dispersion having, when it comprises water, a pH different by at least 1 unit, from the value of the isoelectric point of titanium dioxide in said dispersion, said dispersion further comprising at least one film-forming organic or organosiloxane polymer interacting with the surface of the titanium dioxide particles by electrostatic bonding and selected from the group consisting of:

a sulfonated terephthalic oligoester or copolyester,
a polyoxyalkylenated polymer which carries anionic functions,
a cationic polymer additionally exhibiting bacteriostatic properties,
a cationic homopolymer or copolymer derived from at least one cationic monomer comprising an ethylenic unsaturation, optionally in a mixture with at least one nonionic monomer, and
an amphoteric copolymer derived from at least one cationic monomer comprising an ethylenic unsaturation, and at least one anionic monomer comprising an ethylenic unsaturation, optionally in a mixture with at least one nonionic monomer.

2. A process according to claim 1, wherein the film-forming polymer is selected from the group consisting of:

copolymers of acrylic acid or methacrylic acid and polyethylene glycol acrylate or methacrylate having a polyoxyethylene mass of from 500 to 10,000,
quaternary ammonium ionenes,
cationic polymers derived from epichlorohydrin and dimethylamine, and
cationic polymers derived from epichlorohydrin and imidazole.

3. A process according to claim 1 wherein the cationic monomer comprising an ethylenic unsaturation is selected from the group consisting of:

aminoacryloyl or -acryloyloxy monomers,
N,N-dialkyldiallylamine monomers
polyquaternary monomers.

4. A process according to claim 3 wherein the cationic monomer comprising an ethylenic unsaturation is selected from the group consisting of:

trimethylaminopropyl methacrylate chloride, trimethylaminoethylacrylamide or trimethylaminomethacrylamide chloride or bromide, trimethylaminobutylacrylamide or trimethylaminobutylmethacrylamide methyl sulfate, trimethylaminopropyl-methacrylamide methyl sulfate (MES), (3-methacrylamidopropyl) trimethylammonium chloride (MAPTAC), (3-acrylamidopropyl)trimethylammonium chloride (APTAC), methacryloyloxyethyl trimethylammonium chloride or methyl sulfate, acryloyloxyethyltrimethylammonium chloride, 1-ethyl-2-vinylpyridinium bromide, 1-ethyl-2-vinylpyridinium chloride, 1-ethyl-2-vinylpyridinium bromide methyl sulfate, N,N-dimethyldiallylammonium chloride (DADMAC), dimethylaminopropylmethacrylamide chloride, and N-(3-chloro-2-hydroxypropyl)trimethylammonium (DIQUAT).

5. A process according to claim 1 wherein the anionic monomer comprising an ethylenic unsaturation is selected from the group consisting of:

acrylic, methacrylic, fumaric, maleic, itaconic, N-methacroylalanine, or
N-acryloylhydroxyglycine acids or anhydrides, or their water-soluble salts, and
water-soluble sulfonated or phosphonated ethylenically unsaturated monomers.

6. A process according to claim 5 wherein the anionic monomer comprising an ethylenic unsaturation is selected from the group consisting of:

sulfopropyl acrylate, its water-soluble salts, water-soluble styrenesulfonates, vinylsulfonic acid, its water-soluble salts, vinylphosphonic acid, and its water-soluble salts.

7. A process according to claim 1 wherein the nonionic monomer is selected from the group consisting of acrylamide, N-isopropylacrylamide, N,N- dimethylacrylamide, dimethylaminoethylmethacrylate (DMAEMA), dimethylaminopropylmethacrylamide, vinyl alcohols, alkyl acrylates or methacrylates, hydroxyalkyl acrylates or methacrylates, and polyoxyalkylene glycol acrylates or methacrylates.

8. The process as claimed in claim 1 wherein the cationic or amphoteric polymer derived from at least one cationic monomer comprising an ethylenic unsaturation is selected from the group consisting of:
 a DIQUAT homopolymer;
 a DADMAC homopolymer;
 a MAPTAC/acrylic or methacrylic acid; a DIQUAT/acrylic or methacrylic acid; a DADMAC/acrylic or methacrylic acid copolymer;
 a MES/acrylic or methacrylic acid/DMAEMA copolymer;
 a MAPTAC/acrylic acid/acrylamide; a MAPTAC/maleic anhydride/acrylamide; a MAPTAC/vinylsulfonic acid/acrylamide copolymer;
 a DADMAC/acrylic acid/acrylamide; a DADMAC/maleic anhydride/acrylamide; a DADMAC/vinylsulfonic acid/acrylamide copolymer;
 a DIQUAT/acrylic acid/acrylamide; a DIQUAT/maleic anhydride/acrylamide; and a DIQUAT/vinylsulfonic acid/acrylamide copolymer; copolymers having a ratio of the total number of anionic charges to the total number of cationic charges of from 95/5 to 5/95.

9. A process according to claim 8 wherein the ratio is from 90/10 to 10/90.

10. A process according to claim 1 wherein the dispersion comprises from 0.01 to 2% by weight of the film-forming polymer interacting with the surface of the titanium dioxide particles by electrostatic bonding.

11. A process according to claim 1, wherein the dispersion comprises water and has a pH of from 4 to 9.

12. A film-forming dispersion comprising:
 from 0.01 to 15% of its weight of titanium dioxide in the form of elementary particles whose size is less than 100 nm, and whose specific surface area is greater than 150 $m^2/g$,
 from 0.005 to 15% of its weight of at least one film-forming polyalkoxylated organosiloxane or organic polymer, and
 a continuous phase of said dispersion comprising water or at least one alcohol whose boiling point is less than 120° C., and having, when it comprises water, a pH different by at least 1 unit, from the value of the isoelectric point of titanium dioxide in said dispersion, and the film-forming polymer interacts with the surface of the titanium dioxide particles by electrostatic bonding and is selected from the group consisting of:
 a sulfonated terephthalic oligoester or copolyester,
 a polyoxyalkylenated polymer which carries anionic functions,
 a cationic polymer additionally exhibiting bacteriostatic properties,
 a cationic homopolymer or copolymer derived from at least one cationic monomer comprising an ethylenic unsaturation, optionally in a mixture with at least one nonionic monomer, and
 an amphoteric copolymer derived from at least one cationic monomer comprising an ethylenic unsaturation, and at least one anionic monomer comprising an ethylenic unsaturation, optionally in a mixture with at least one nonionic monomer.

13. A film-forming dispersion according to claim 12 wherein the film-forming polymer is selected from the group consisting of:
 copolymers of acrylic acid or methacrylic acid and polyethylene glycol acrylate or methacrylate having a polyoxyethylene mass of from 500 to 10,000,
 quaternary ammonium ionenes,
 cationic polymers derived from epichlorohydrin and dimethylamine, and
 cationic polymers derived from epichlorohydrin and imidazole.

14. A film-forming dispersion according to claim 12 wherein the cationic monomer comprising an ethylenic unsaturation is selected from the group consisting of:
 aminoacryloyl or -acryloyloxy monomers,
 N,N-dialkyldiallylamine monomers
 polyquaternary monomers.

15. A film-forming dispersion according to claim 14 wherein the cationic monomer comprising an ethylenic unsaturation is selected from the group consisting of:
 trimethylaminopropyl methacrylate chloride, trimethylamninoethylacrylamide or trimethylaminomethacrylamide chloride or bromide, trimethylaminobutylacrylamide or trimethylaminobutylmethacrylamnide methyl sulfate, trimethylaminopropyl-methacrylamide methyl sulfate (MES), (3-methacrylamidopropyl)trimethylammonium chloride (MAPTAC), (3-acrylamidopropyl)trimethylammonium chloride (APTAC), methacryloyloxyethyl trimethylammonium chloride or methyl sulfate, acryloyloxyethyltrimethylammonium chloride, 1-ethyl-2-vinylpyridinium bromide, 1-ethyl-2-vinylpyridinium chloride, 1-ethyl-2-vinylpyridinium bromide methyl sulfate, N,N-dimethyldiallylammonium chloride (DADMAC), dimethylaminopropylmethacrylamide chloride, and N-(3-chloro-2-hydroxypropyl)trimethylammonium (DIQUAT).

16. A film-forming dispersion according to claim 12 wherein the anionic monomer comprising an ethylenic unsaturation is selected from the group consisting of:
 acrylic, methacrylic, fumaric, maleic, itaconic, N-methacroylalanine, or N-acryloylhydroxyglycine acids or anhydrides, or their water-soluble salts, and
 water-soluble sulfonated or phosphonated ethylenically unsaturated monomers.

17. A film-forming dispersion according to claim 16 wherein the anionic monomer comprising an ethylenic unsaturation is selected from the group consisting of:
 sulfopropyl acrylate, its water-soluble salts, water-soluble styrenesulfonates, vinylsulfonic acid, its water-soluble salts, vinylphosphonic acid, and its water-soluble salts.

18. A film-forming dispersion according to claim 12 wherein the nonionic monomer is selected from the group consisting of acrylamide, N-isopropylacrylamide, N,N-dimethylacrylamide, dimethylaminoethylmethacrylate (DMAEMA), dimethylaminopropylmethacrylamide, vinyl alcohols, alkyl acrylates or methacrylates, hydroxyalkyl acrylates or methacrylates, and polyoxyalkylene glycol acrylates or methacrylates.

19. A film-forming dispersion according to claim 12 wherein the cationic or amphoteric polymer derived from at least one cationic monomer comprising an ethylenic unsaturation is selected from the group consisting of:
 a DIQUAT homopolymer;
 a DADMAC homopolymer;

a MAPTAC/acrylic or methacrylic acid; a DIQUAT/acrylic or methacrylic acid; a DADMAC/acrylic or methacrylic acid copolymer;

a MES/acrylic or methacrylic acid/DMAEMA copolymer;

a MAPTAC/acrylic acid/acrylamide; a MAPTAC/maleic anhydride/acrylamide; a MAPTAC/vinylsulfonic acid/acrylamide copolymer;

a DADMAC/acrylic acid/acrylamide; a DADMAC/maleic anhydride/acrylamide; a DADMAC/vinylsulfonic acid/acrylamide copolymer;

a DIQUAT/acrylic acid/acrylamide; a DIQUAT/maleic anhydride/acrylamide; and a DIQUAT/vinylsulfonic acid/acrylamide copolymer; copolymers having a ratio of the total number of anionic charges to the total number of cationic charges of from 95/5 to 5/95.

20. A film-forming dispersion according to claim 19 wherein the ratio is from 90/10 to 10/90.

21. A film-forming dispersion according to claim 12, wherein the dispersion comprises from 0.01 to 2% by weight of the film-forming polymer interacting with the surface of the titanium dioxide particles by electrostatic bonding.

22. A film-forming dispersion according to claim 12, wherein the dispersion comprises water and has a pH of from 4 to 9.

* * * * *